United States Patent [19]

Copp

[11] Patent Number: 4,628,554

[45] Date of Patent: Dec. 16, 1986

[54] COLLAPSIBLE SUPPORT USED DURING COLONIC IRRIGATION

[76] Inventor: Roy A. Copp, P.O. Box 43, Banglamung Chonburi 20150, Thailand

[21] Appl. No.: 776,795

[22] Filed: Sep. 17, 1985

[51] Int. Cl.[4] ........................ A61G 7/02; A61M 31/00

[52] U.S. Cl. ........................ 5/90; 5/68; 269/327; 604/276; D24/51

[58] Field of Search ........................ 5/90, 62, 66, 67, 68, 5/69; 269/322-328, 13, 15; 128/70-74; 4/443, 445, 327, 559, 571, 573, DIG. 5; D24/51, 53, 54, 60; 604/276

[56] References Cited

U.S. PATENT DOCUMENTS

| | | | |
|---|---|---|---|
| D. 262,656 | 1/1982 | Johnson | D24/51 |
| D. 264,881 | 6/1982 | Shaffer | D24/51 |
| 470,251 | 3/1892 | Morrison | 5/90 X |
| 692,061 | 1/1902 | McCullough | 5/90 X |
| 1,471,258 | 10/1923 | Glines | 269/327 |
| 1,945,081 | 1/1934 | Ryan et al. | 269/327 |
| 1,958,100 | 5/1934 | Borosini | 604/276 |
| 1,998,061 | 4/1935 | Wachs | 5/90 X |
| 2,133,626 | 10/1938 | Mayberry | 604/276 |
| 2,176,235 | 10/1939 | Woodard | 604/276 X |
| 2,564,135 | 8/1951 | Touchberry | 604/276 X |
| 2,852,025 | 9/1958 | Wessels | D24/51 X |
| 4,307,477 | 12/1981 | Jacobsen | 5/90 X |

FOREIGN PATENT DOCUMENTS

| | | | |
|---|---|---|---|
| 634229 | 2/1928 | France | 604/276 |
| 603530 | 6/1948 | United Kingdom | 5/90 |

*Primary Examiner*—William F. Pate, III
*Assistant Examiner*—Richard Chilcot
*Attorney, Agent, or Firm*—James D. Thackrey

[57] ABSTRACT

A support for the prone back during an upper enema, in which the legs are folded, with the feet resting on footrests and the buttocks adjacent to an effluent shield which stops the effluent and allows it to drop into a toilet, on which the lower part of the support rests. The support is collapsible for transport or storage, as is a stand which is beneath the center of gravity of body plus support. This stand makes contact with the support on both sides of the center of gravity. At discharge it and the toilet bowl span the center of gravity; during the enema the patient may, by manipulating a lever, raise the buttock part of the support by means of a linkage as desired in order to produce a more thorough irrigation of the colon. Provision is also made for increasing colonic reaction by color and by reflexology prods on the soles of the feet.

2 Claims, 3 Drawing Figures

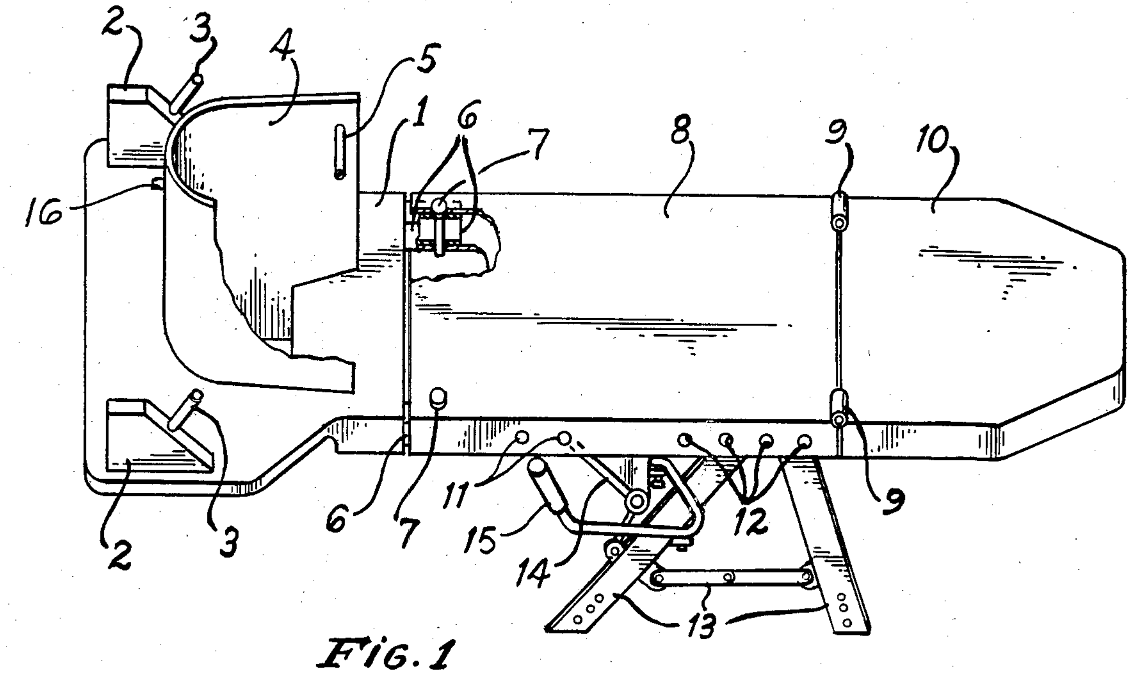
FIG. 1
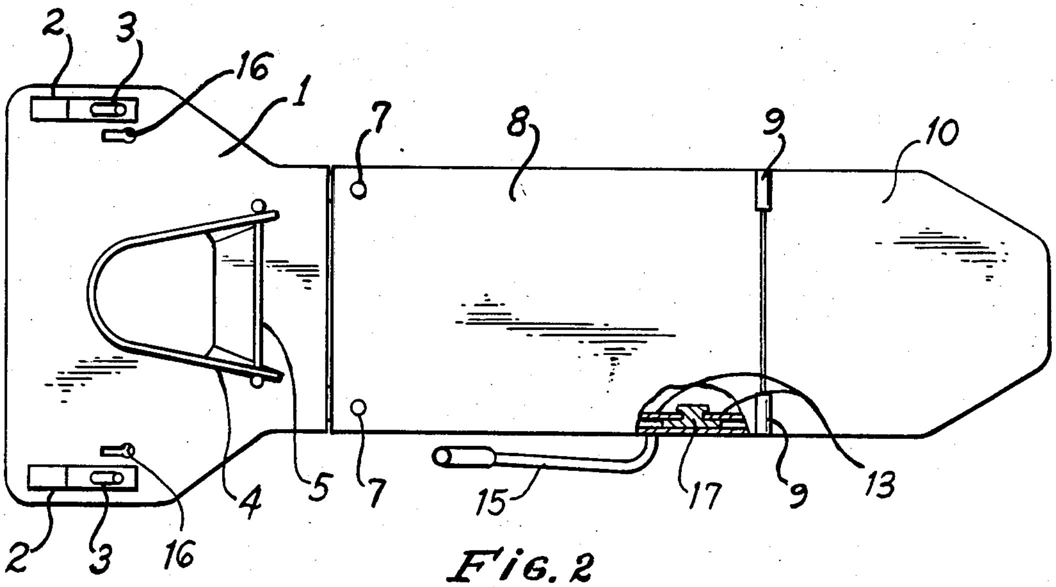
FIG. 2
FIG. 3
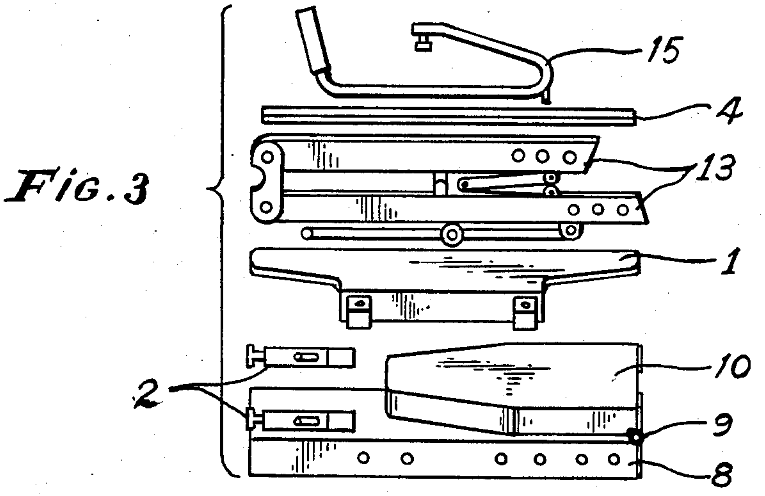

COLLAPSIBLE SUPPORT USED DURING COLONIC IRRIGATION

BACKGROUND OF THE INVENTION

1. Field of the Invention

Ordinary or lower enemas lave the bowel with treated water and so cleanse it. High enemas involve the colon as well as the bowel, and this invention is in that field. It helps perform and control the enema procedure to the extent that it is better described as colonic irrigation. Specifically, the invention is a support for the patient to lie on while receiving a high enema—ordinarily it would be self-administered.

2. Description of Prior Art

The art of supporting the patient during a high enema has not received very much attention. A patient lying on a bed with a bedpan under his rectum is typical. Recently, special boards have been marketed which allow the patient to place his hips in a comfortable position aligned with his torso, and which direct the effluent under a corner into a toilet. These supports are cumbersome to handle and to clean and they are normally used only at one body angle.

SUMMARY OF THE INVENTION

The invention offers collapsibility and ready cleanability to overcome the drawbacks of the present art combining also two features which enhance the effectiveness of the upper enema experience. These are provision of reflexivity prods and footrests supplied for the feet, and provision for tilting the body so as to get improved circulation of the laving treated water during the retention phase. Thus the object of the invention is to provide more convenience and improved operation of supports for use during high enema/colonic irrigation.

The invention is like a narrow bed on which the patient lies on his back with his knees drawn up and his feet separated. The portion of the bed below the patient's buttocks is removable for cleaning, and contains a deflector shield which directs the effluent matter from a horizontal to a downward path, through the bed and into a toilet on which part of the bed rests. This part of the bed has footrests containing reflexivity prods to bear on the pressure points in the patient's feet which stimulate the colon. The footrests may be removable for cleaning.

The portion of the bed under the patient's back and head is foldable to make it easy to store and carry. An adjustable stand supports this part in two alternate manners. During discharge the stand supports the bed and body just above (toward the head from) the center of gravity. During preparation the stand also supports bed and body just below the center of gravity. When this second, lower support is provided the bed is tilted so the buttocks are higher than the head. There is a lever which operates on the stand so the patient may select which manner of support he desires and may rapidly shift between them.

BRIEF DESCRIPTION OF THE DRAWINGS

FIG. 1 is the invention as viewed from a position between side and top view.

FIG. 2 is from the same perspective as is FIG. 1, but is a view looking directly down on the invention as it would be configured for use.

FIG. 3 is a view in slight perspective of the parts as they fit together in a collapsed position for transporting or storage.

DETAILED DESCRIPTION OF THE INVENTION

Although one of the novel characteristics of the invention is its collapsibility, the invention as a whole is best illustrated in FIG. 1. Extension portion 1 and attachment means 6 are shown in the preferred embodiments. Attachment means 6, as shown, is permanently fixed to extension portion 1 and enters sockets which are a part of the collapsible support portion, made up of center section 8, hinge 9, and headrest portion 10. As shown in FIG. 1, attachment means 6, when in the socket formed for it in center section 8, is held securely by pins 7. Hence a patient with his torso on the collapsible support portion and his feet resting on footrests 2, may exert pressure by straightening his folded leg without causing 1 and 8 to separate. Yet 1 and 8 may easily be separated and 1 cleaned as required after the high enema is complete.

In order to reach pressure points in the feet to which the colon responds, bearing pins or reflexive prods 3 are attached to footrests 2 in the preferred embodiment. It is also preferred, in order to simplify cleaning and collapsing, to have footrests 2 be removable. This is accomplished by providing keyhole-shaped slots 16 in extension portion 1. Various spread angles of the patient's feet may be reached by providing several progressively wider-spaced sets of keyhole-shaped slots 16 in extension portion 1. A headed protrusion on footrest 2 can then be locked into the keyhole-shaped slots 16 for ready installation or removal of footrests 2. Other quick and easily cleaned joining means would obviously be suitable, but the arrangement described is the preferred embodiment.

A splash director shield 4 is shown at right angles to extension portion 1. This is a flat sheet of material in the preferred embodiment, sprung into a U shape with guywire 5 preventing springback of the top portion (the second part) of the shield. The bottom portion (the first part) is forced into a formed cutout in extension portion 1. Thus shield 4 tends to fit tightly in the formed cutout, and as it also protrudes through 1 it is held securely in 1 by its own self-flattening tendency. The upper surface of extension portion 1 is sloped downward toward the opening which receives shield 4 in the preferred embodiment, which also tends to hold shield 4 firmly.

Center section 8 rests on a pivot point 17, the location of which may be individualized by the patient's choosing two of the series of holes 12 to mount the pivot point. A pivot groove (such as a journal partially around a shaft) is part of collapsible stand 13. This arrangement is illustrated in FIG. 2. The center of gravity of patient plus bed lies slightly to the left of 17 in FIG. 2, and to the right of holes 11 in FIG. 1. Thus when the links of pin-jointed spreader 14 are forced into colinearity by lever means 15 the entire bed is tilted, extension portion 1 being lifted from the toilet and all weight being now supported by collapsible stand 13. The effectiveness of the upper enema is greatly increased by the head-down tilted position and by the sloshing during change in tilt. To individualize the support, the point at which the pin-jointed spreader 14 engages center section 8 is adjustable by selection during assembly among the holes 11. The pin-jointed spreader is similar to that used between the legs of folding step-ladders. In the preferred embodiment the link elements of spreader 14 extend across the bed, duplicate holes 11 exist on each side and the point where lever means 15 presses on pin-jointed spreader 14 is under the center of the bed (or center section 8). Lever 15 exerts the force required to straighten 14 by virtue of being pivoted on collapsible stand 13.

FIG. 3 shows the support dismantled, collapsed, and with its parts in the appropriate position for storage or transport. The sizes of parts and location of hinges 9 appropriate for using the support lend themselves well to relatively compact storage. As shown in the figure, the upper body collapsible support portion folds, the extension portion stripped of shield and footrests and turned 90 degrees, fits above it, shield 4, collapsible stand 13, and lever means 15 occupy about the same "plan view" and add to the thickness of the package. Collapsibility for storage in transport is a key part of this inventive combination.

In operation, the patient would set up the invention with extension portion 1 resting on the toilet bowl. Lying on his back on the collapsible support portion (made up of center section 8, hinges 9, and headrest portion 10), he would adjust himself so his buttocks were just short of the toilet bowl and his folded thighs spread around splash director shield 4. This shield is open toward the patient's buttocks, partly protrudes through an opening in extension portion 1, and is open to the toilet. During the upper enema the patient may operate lever means 15 to tilt his body head downward. When he is about to release the enema he operates lever means 15 to rest the lower end of the bed, extension portion 1, on the toilet.

The invention having been described in its preferred embodiment, it is clear that it is susceptible to numerous modifications and embodiments within the ability of those skilled in the art without the exercise of the inventive faculty. Accordingly the scope of this invention is defined by the scope of the following claims.

I claim:

1. A bodyrest for use during a high enema, in which the body is generally horizontal, the legs drawn up, and the buttocks resting above and slightly short of a toilet bowl, comprising:

a collapsible support portion extending from the head to the buttocks, and an extension portion which rests on the toilet bowl, and attachment means connecting said collapsible support portion to said extension portion, and a splash director shield passing through the central part of said extension portion, having a first part protruding through said extension portion, the first part being open toward the toilet, and a second part extending well above said extension portion and being open toward the buttocks, and a collapsible stand supporting said collapsible support portion in a tiltable manner, the support point being closer to the head than is the center of gravity of bodyrest and body, and a pin-jointed spreader attached between the lower part of said collapsible stand and an area on said collapsible support portion beyond the center of gravity of bodyrest and body, of a length such that the buttocks end of said collapsible support portion is lifted when said pin-jointed spreader is straightened, and lever means, pivoted on said collapsible stand, for straightening or collapsing said pin-jointed spreader, whereby the person receiving the enema may manipulate said lever means to tilt his body in order to control events during the enema.

2. A bodyrest for use during a high enema, in which the body is generally horizontal with the buttocks resting above and slightly short of a toilet bowl, comprising:

a collapsible support portion extending from the head to the buttocks, and an extension portion which rests on the toilet bowl, and attachment means connecting said collapsible support portion to said extension portion, and two bearing pins connected to said extension portion near the extreme transverse edges and positioned above the surface of said extension portion with the axis pointing toward the head end of said collapsible support portion, said bearing pins being used to apply pressure below the surface of the feet, and a splash director shield passing through the central part of said extension portion, having a first part protruding through said extension portion, the first part being open toward the toilet, and a second part extending well above said extension portion and being open toward the buttocks, and a collapsible stand supporting said collapsible support portion in a tiltable manner, the support point being closer to the head than is the center of gravity of bodyrest and body, and a pin-jointed spreader attached between the lower part of said collapsible stand and an area on said collapsible support portion beyond the center of gravity of bodyrest and body, of a length such that the buttocks end of said collapsible support portion is lifted when said pin-jointed spreader is straightened, and lever means, pivoted on said collapsible stand, for straightening or collapsing said pin-jointed spreader, whereby the person receiving the enema may manipulate said lever means to tilt his body and may apply pressure to control regions within his feet in order to control events during the enema.

* * * * *